(12) United States Patent
Botero

(10) Patent No.: US 7,844,316 B1
(45) Date of Patent: Nov. 30, 2010

(54) EKG CABLE

(76) Inventor: Carlos A Botero, 1507 W. Reynolds St., Suite A, Plant City, FL (US) 33563

( * ) Notice: Subject to any disclaimer, the term of this patent is extended or adjusted under 35 U.S.C. 154(b) by 1073 days.

(21) Appl. No.: 11/585,311

(22) Filed: Oct. 23, 2006

(51) Int. Cl.
*A61B 5/0402* (2006.01)

(52) U.S. Cl. .................. 600/386; 600/393; 600/509; 439/909

(58) Field of Classification Search .............. 600/386, 600/393, 509; 439/909
See application file for complete search history.

(56) References Cited

U.S. PATENT DOCUMENTS

| | | | |
|---|---|---|---|
| 4,328,814 A | 5/1982 | Arkans | |
| 4,353,372 A * | 10/1982 | Ayer | 600/393 |
| 4,573,474 A * | 3/1986 | Scibetta | 600/382 |
| 4,854,323 A | 8/1989 | Rubin | |
| 4,957,109 A | 9/1990 | Groeger et al. | |
| 5,203,720 A | 4/1993 | Zini | |
| 5,341,806 A | 8/1994 | Gadsby et al. | |
| 5,546,950 A | 8/1996 | Schoeckert et al. | |
| 5,813,404 A | 9/1998 | Devlin et al. | |
| 6,076,003 A | 6/2000 | Rogel | |
| 6,415,169 B1 | 7/2002 | Kornrumpf et al. | |
| 6,891,379 B2 | 5/2005 | Kelly et al. | |
| 7,021,960 B2 * | 4/2006 | Ubby et al. | 439/505 |
| 7,197,357 B2 * | 3/2007 | Istvan et al. | 600/509 |
| 7,277,743 B2 * | 10/2007 | Brodnick | 600/382 |
| 2003/0191401 A1 * | 10/2003 | Oury et al. | 600/509 |

FOREIGN PATENT DOCUMENTS

| | | |
|---|---|---|
| FR | 2.531.330 | 2/1984 |
| FR | 2.831.046 | 4/2003 |

* cited by examiner

*Primary Examiner*—Lee S Cohen
(74) *Attorney, Agent, or Firm*—Michael I Kroll

(57) ABSTRACT

The present invention relates to an EKG cable for connection to an EKG machine. The cable has a root cable with a connector for connection to the EKG machine. The root cable is connected to a cable connector. The cable connector has at least two branch cables connected thereon. Each of the branch cables has a plurality of nodes disposed thereon. Each of the nodes has two connections each being capable of being connected to an electrode disc. Each of the nodes have opposing upper and lower surface. Each of the surfaces may have indicia disposed thereon. Each of the surfaces may be color-coded. The indicia and the color-coding may be used independently of each other or in combination with each other.

19 Claims, 8 Drawing Sheets

EKG CABLE

BACKGROUND OF THE INVENTION

1. Field of the Invention

Figure 1:
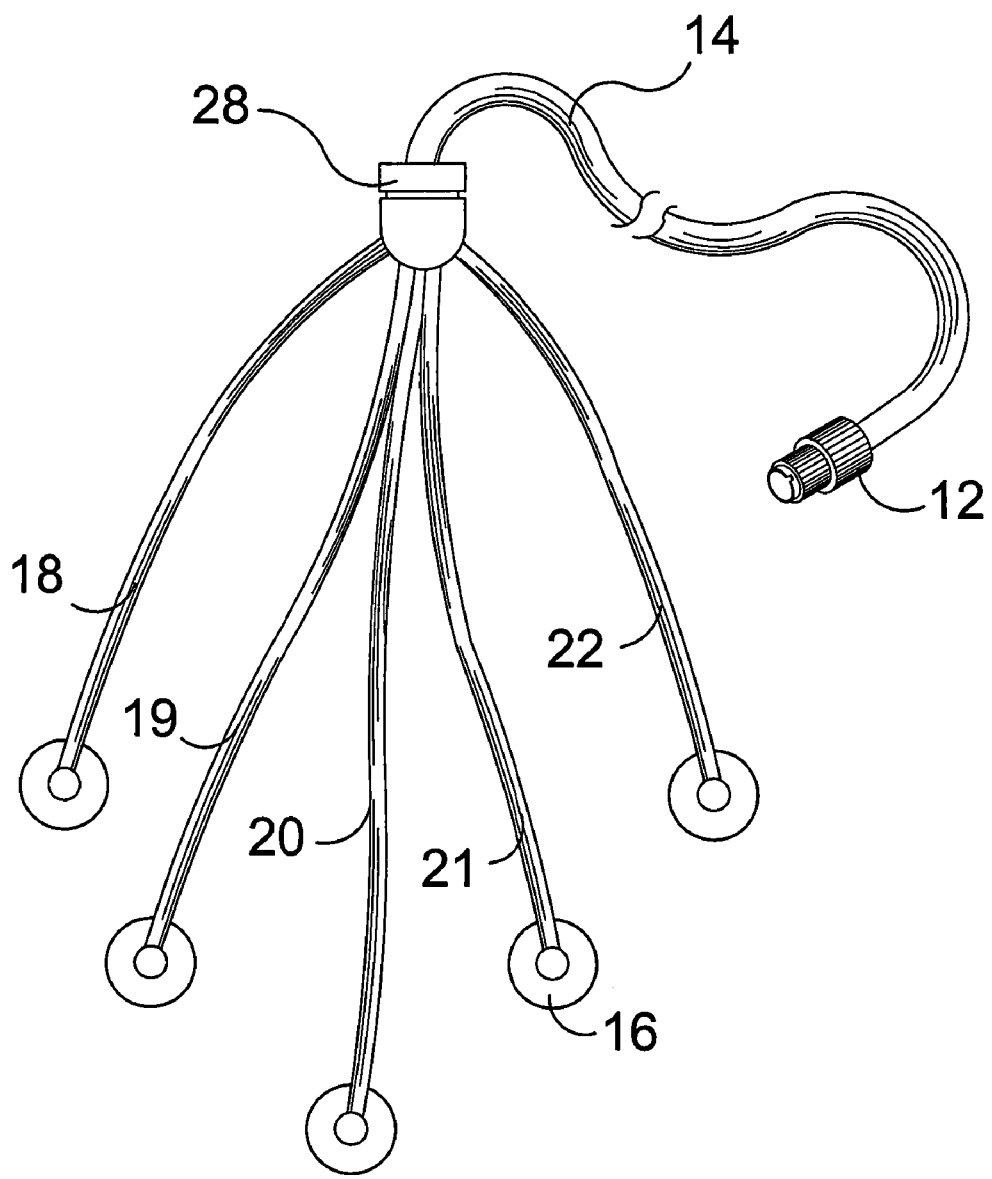

The present invention relates generally to cables and, more specifically, to an EKG cable having a pair of leads wherein a first lead has an electrical connection node positioned approximate the distal end with a second similar node spaced away an approximate distance and a third node spaced from the second a predetermined distance. Along with the second lead having a pair of spaced electrical connection nodes, which provide an EKG cable having five electrical connection nodes appropriately positioned on the pair of leads.

2. Description of the Prior Art

There are other cable devices designed for EKG machines. Typical of these is U.S. Pat. No. 4,328,814 issued to Arkans on May 11, 1982.

Another patent was issued to Rubin on Aug. 8, 1989 as U.S. Pat. No. 4,854,323. Yet another U.S. Pat. No. 4,957,109 was issued to Groeger et al. on Sep. 18, 1990 and still yet another was issued on Apr. 20, 1993 to Zini as U.S. Pat. No. 5,203,720.

Another patent was issued to Gadsby, et al. on Aug. 30, 1994 as U.S. Pat. No. 5,341,806. Yet another U.S. Pat. No. 5,546,950 was issued to Schoeckert, et al. on Aug. 20, 1996. Another was issued to Devlin, et al. on Sep. 29, 1998 as U.S. Pat. No. 5,813,404 and still yet another was issued on Jun. 13, 2000 to Rogel as U.S. Pat. No. 6,076,003.

Another patent was issued to Kornrumpf, et al on Jul. 2, 2002 as U.S. Pat. No. 6,415,169. Yet another U.S. Pat. No. 6,891,379 was issued to Kelly, et al. on May 10, 2005. Another was issued to Robert on Feb. 10, 1984 as French Patent No. FR2531330.

U.S. Pat. No. 4,328,814

Inventor: Edward J. Arkans

Issued: May 11, 1982

A precordial ECG strip comprising, a plurality of electrode assemblies with each comprising a housing having a front surface, a recess received in the front surface of the housing, an ECG electrode received in an inner part of the recess, and a conductive lead having one end electrically connected to the electrode. The electrode assemblies are connected together in a row with the leads of the electrode assemblies extending along the row of the electrode assemblies U.S. Pat. No. 4,854,323

Inventor: Lawrence A. Rubin

Issued: Aug. 8, 1989

An electrode harness for an electrocardiograph apparatus has a hollow tube for containing and housing the individual lead wires for each electrode and a flexible stylet which when bent, into a desired shape, will maintain that shape, until reshaped. The individual electrodes are slidably adjustable about the exterior of the hollow tube to enhance precise positioning of the electrodes to thereby maximize the proper recording of electro-cardiac information from the patient. All of the individual lead wires are bundled together and exit from the hollow tube at a single location. In addition, the electrical plug for the harness is uniquely configured so that it can only be plugged into the corresponding female receptacle of the electrocardiograph recording machine in the proper manner. The harness is also provided with a pair of straps which are adapted to be placed beneath the right shoulder and the left hip of the patient. The weight of the tube and/or stylet also provides a downward bias of the harness towards the skin surface of the patient to maximize electrical contact between electrodes and patient.

U.S. Pat. No. 4,957,109

Inventor: Jeffrey Groeger, et al.

Issued: Sep. 18, 1990

An electrode assembly for acquiring physiological signals, comprising a flexible substrate having a bottom surface and a top surface, means forming a plurality of electrodes at the bottom surface of the substrate and each electrode having a bottom surface facing away from the substrate, an electrical connector fixed to the substrate and having a plurality of connector elements, a plurality of flexible conductors fixed on the substrate and connecting the electrodes to the connector elements, a layer of conductive adhesive on the bottom surface of each electrode; and an adhesive layer on at least a portion of the bottom surface of the substrate.

U.S. Pat. No. 5,203,720

Inventor: Roberto Zini

Issued: Apr. 20, 1993

A connecting cable uses a multiple-core, multiple-screen strap which is provided at one end with a terminal (6) within which are dischargers (12) for protection against excess voltages and with a connector (13) for removable connection to the electrocardiograph. At two intermediate points, with a suitable distance between them, the strap is provided with clamps (7-8) from which are branched separate leads for the peripheral and precodial branches. The leads are provided at their free ends with plugs (9) for connection to measuring electrodes, and electrical resistors for protection against excess voltages are preferably housed in the bodies of the plugs.

U.S. Pat. No. 5,341,806

Inventor: Peter D. Gadsby, et al.

Issued: Aug. 30, 1994

Disclosed is an electrode strip (100) for use in electrocardiography comprising a flexible and substantially inextendible substrate (104), a plurality of conductors (114) that extend along the substrate to form a plurality of electrode sites (V.sub.1-V.sub.6, RA, LA, LL, RL), and a cover layer (122) that insulates the conductors. A plurality of regions of extensibility (102) in the strip allow selective positioning of the electrode sites on a body.

U.S. Pat. No. 5,546,950

Inventor: Kurt P. Schoeckert

Issued: Aug. 20, 1996

An electrocardiographic patient lead cable apparatus comprises an elongated cable part and a connector. The cable part has a plurality of connecting wires with connectors for the electrodes. The connecting wires are joined together for varying portions of their length to form a flat common portion of the cable part. The common portion is connected at one end to the connector. The connecting wires separate from the common portion at the selected locations along the extension of the common part from the end connected to the connector to form relatively short separated connecting wires. The lead cable apparatus so formed facilitates correct connection of electrodes positioned at various locations on the body of the patient and reduces or eliminates tangling of the connecting wires. The connector is of compact, lightweight construction.

U.S. Pat. No. 5,813,404

Inventor: Phillip H. Devlin, et al.

Issued: Sep. 29, 1998

Disclosed is a physiological electrical signal connector system which one connector connected to an electrode set and another connector connected to a digital signal convertor which leads to a patient monitor. Each type of electrode set has a specific code identified with it and when connected to the digital signal convertor, the connector code is recognized by the digital signal convertor. The connector code is then relayed to the monitor which will self-configure based on the identified code.

U.S. Pat. No. 6,076,003

Inventor: Dan Rogel

Issued: Jun. 13, 2000

(An electrocardiography electrodes holder featuring (a) a flexible nonconductive flattened body having a fixed precordial configuration, the body featuring a first plane and an opposite second plane; (b) six electrocardiography electrode accepting holes formed in the flexible nonconductive flattened body traversing the planes for respectively engaging six electrocardiography electrodes, each of the six electrode accepting holes featuring a conductive inner circumference, the electrode accepting holes being located in a predetermined pattern effective for the precordial electrocardiography recordings; (c) six conductive recording lines electrically communicating with the conductive inner circumference of the six electrode accepting holes, the six conductive lines being on the second plane of the flexible nonconductive flattened body; (d) a first set of six conductive grounding lines, each being associated with one of the six conductive recording lines for electrically shielding the six conductive recording lines; (e) at least one terminal for electrically connecting the six conductive recording lines to a cardiometer and for grounding the conductive grounding lines. The electrocardiography electrodes holder can be a part of a set further including electrocardiography electrodes, a holding strap and a cardiometer.

U.S. Pat. No. 6,415,169

Inventor: William P. Kornrumpf, et al.

Issued: Jul. 2, 2002

A flexible multiple electrode assembly includes at least one fixed electrode; at least one extendible electrode; and electrically conductive interconnections coupling the at least one fixed electrode and the at least one extendible electrode to a common connector. The at least one extendible electrode is adapted to be physically separable from the at least one fixed electrode while remaining electrically coupled to the common connector. In one embodiment, an array of fixed and extendible electrodes is configured for the acquisition of electrical pulses from a heart for transmission to an electrocardiograph (EKG or ECG) device.

U.S. Pat. No. 6,891,379

Inventor: Clifford Mark Kelly, et al.

Issued: May 10, 2005

A wiring harness is provided for conveying signals representing measurements made at a first location to a measuring instrument remotely located from the first location. The harness includes a first cable having an outer sheath with a first diameter and a plurality of coaxial cables arranged within the outer sheath of the first cable. A plurality of contacts is arranged on the outer sheath of the first cable. Each of the contacts is electrically connected to a respective inner conductor of one of the plurality of coaxial cables.

French Patent Number FR2531330

Inventor: Andre Robert

Issued: Feb. 10, 1984

The device comprises at least two electrodes each connected by a flexible conductor to a digital display and is constituted by a belt 1 which can be secured onto the body of an animal and by a band 5 carrying the electrodes 15 and a zig-zag section of the conductor, this band 5 being fixed removably onto the belt 1. By virtue of the elastic parts of the band 5 and of the belt 1, the electrodes 15 are kept in a fixed position on the body of the animal.

While these cables may be suitable for the purposes for which they were designed, they would not be as suitable for the purposes of the present invention, as hereinafter described.

SUMMARY OF THE PRESENT INVENTION

A primary object of the present invention is to provide an EKG cable having split leads with consecutively placed common nodes for connection to electrodes.

Another object of the present invention is to provide an EKG cable having a pair of leads that when extending down the patient torso has three node electrode connections on the right side for left arm (LA), Left leg (LL) and heart (V) and on the left side two nodes for right arm (RA) and right leg (RL).

Yet another object of the present invention is to provide an EKG cable having a pair of leads that when extending up the patient torso has three node electrode connections on the right side for left arm (LA), left leg (LL) and heart (V) and on the left side two nodes for right arm (RA) and right leg (RL).

Yet another object of the present invention is to provide an EKG monitoring cable having five nodes spaced along two wire leads extending from a suitable Electrocardiograpic machine connector.

Still yet another object of the present invention is to provide an EKG cable that eliminates the need for a plurality of separate cables extending from said common Electrocardiograpic machine connector to each of the electrical signal recording locations (LA, LL, V, RA and RL)

Additional objects of the present invention will appear as the description proceeds.

The present invention overcomes the shortcomings of the prior art by providing an EKG cable having a pair of leads wherein a first lead has an electrical connection node positioned approximate the distal end with a second similar node spaced away an approximate distance and a third node spaced from the second a predetermined distance. Along with the second lead having a pair of spaced electrical connection nodes, which provide an EKG cable having five electrical connection nodes approximately positioned on the pair of leads.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

Figure 2:
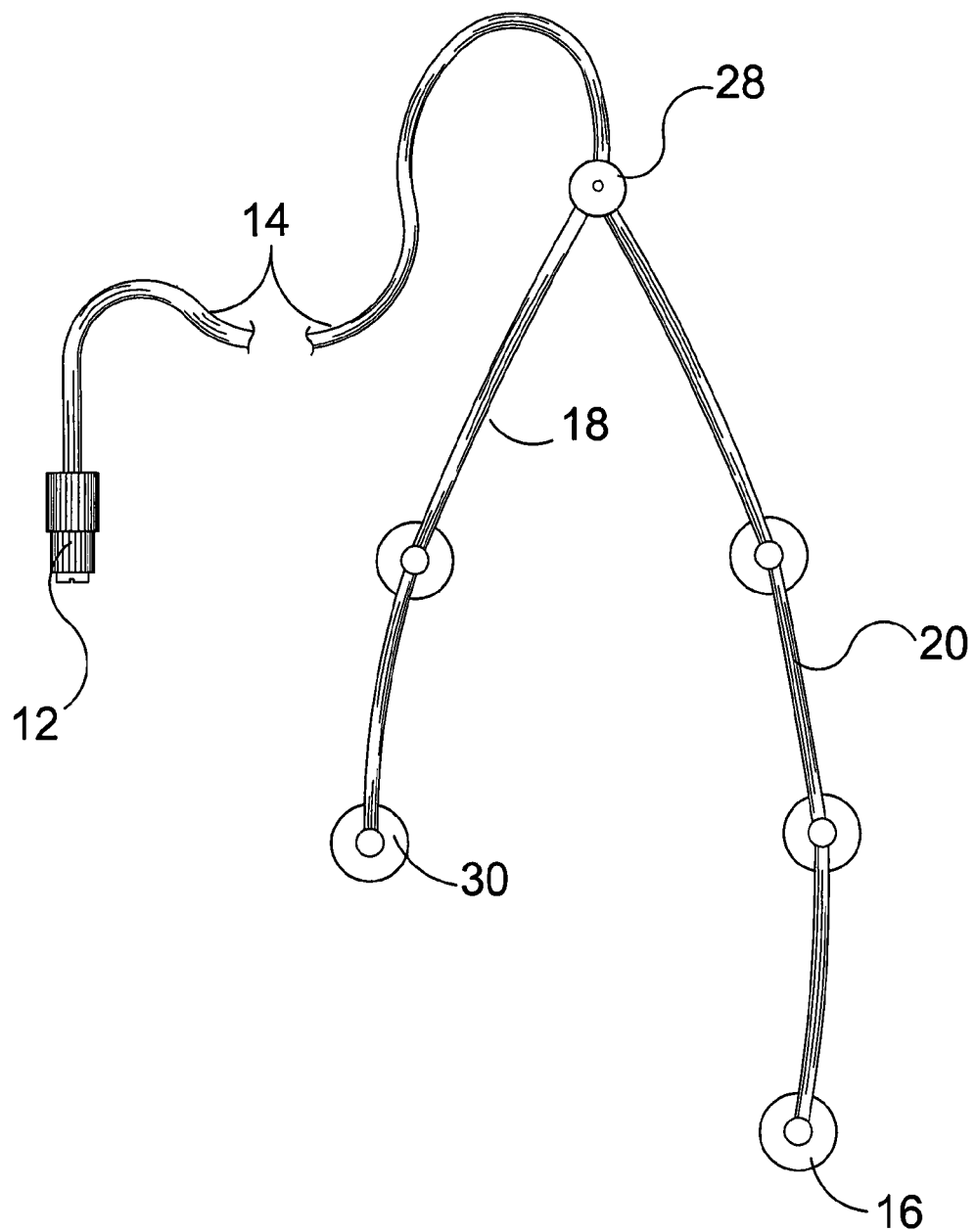
Figure 3:
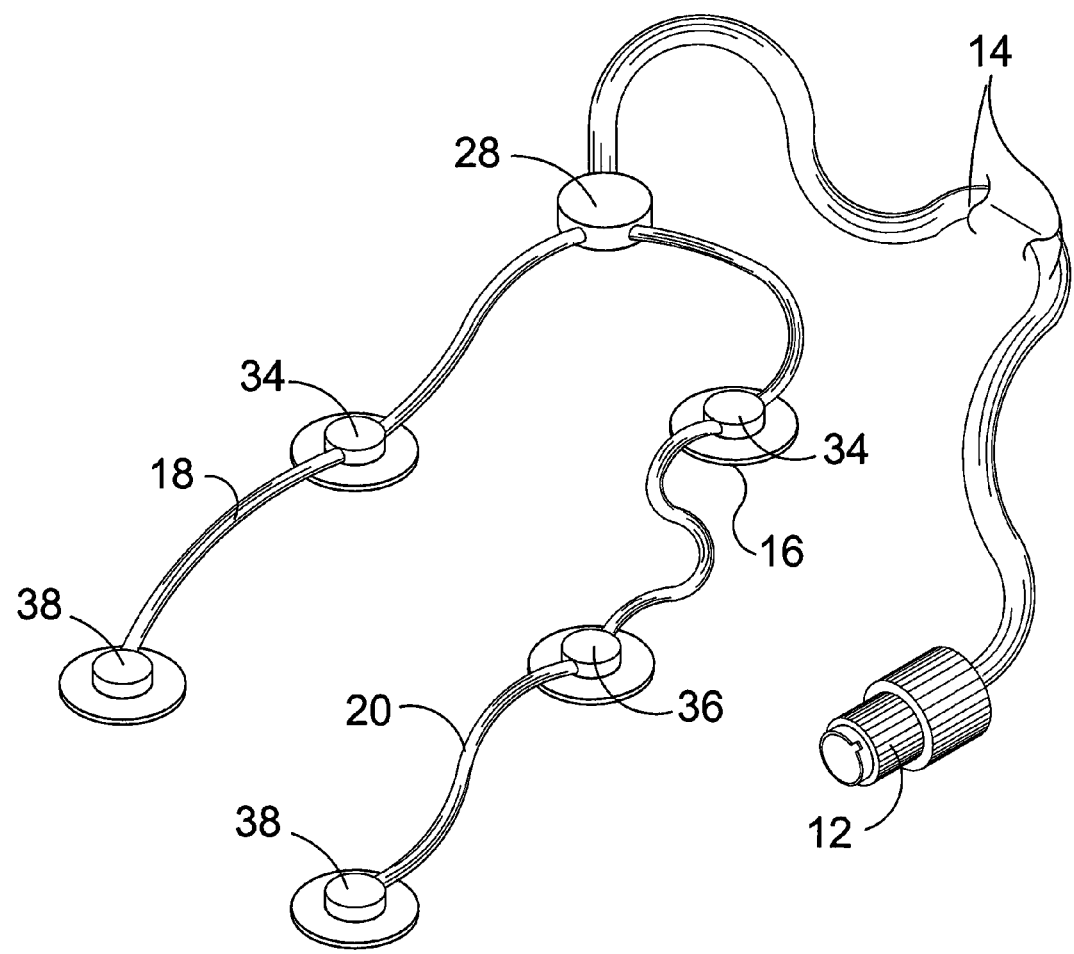
Figure 4:
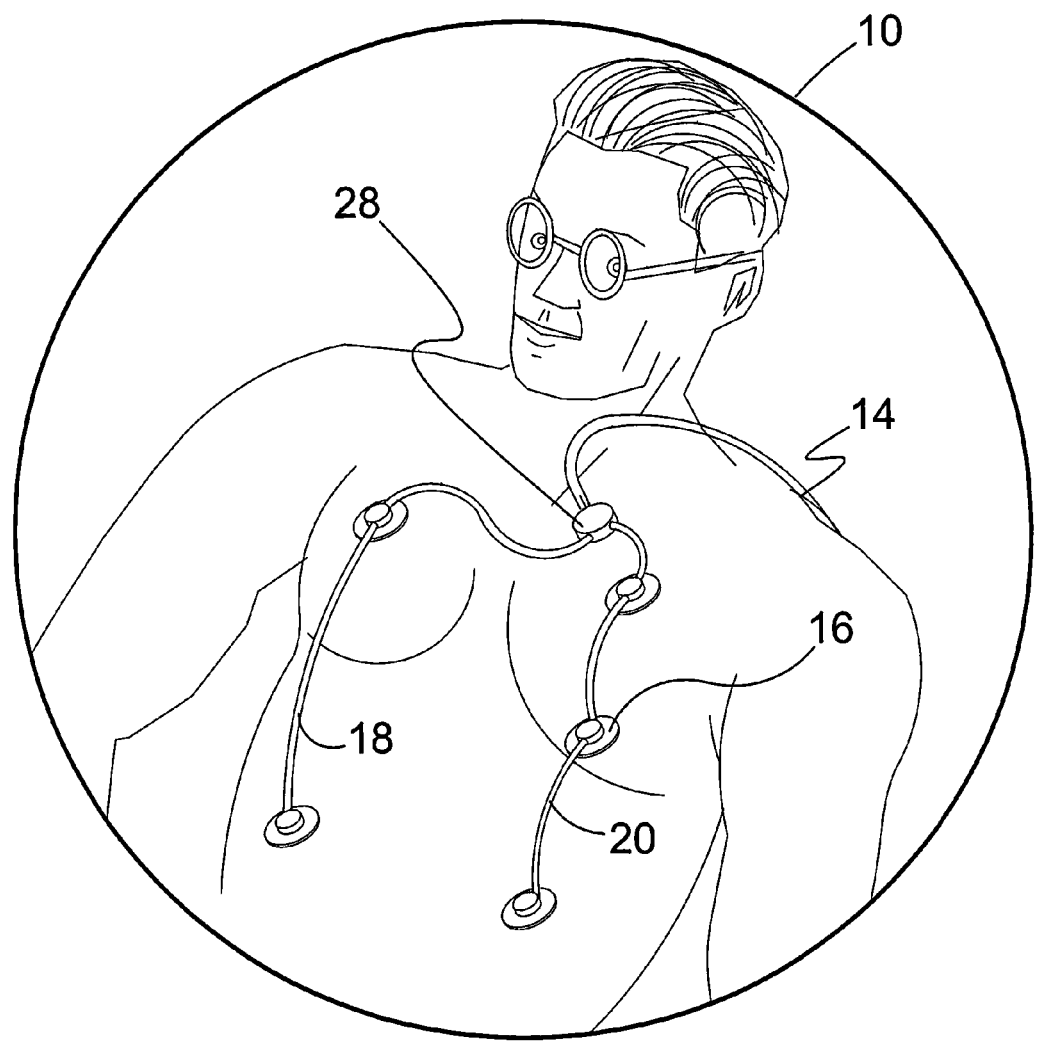
Figure 5:
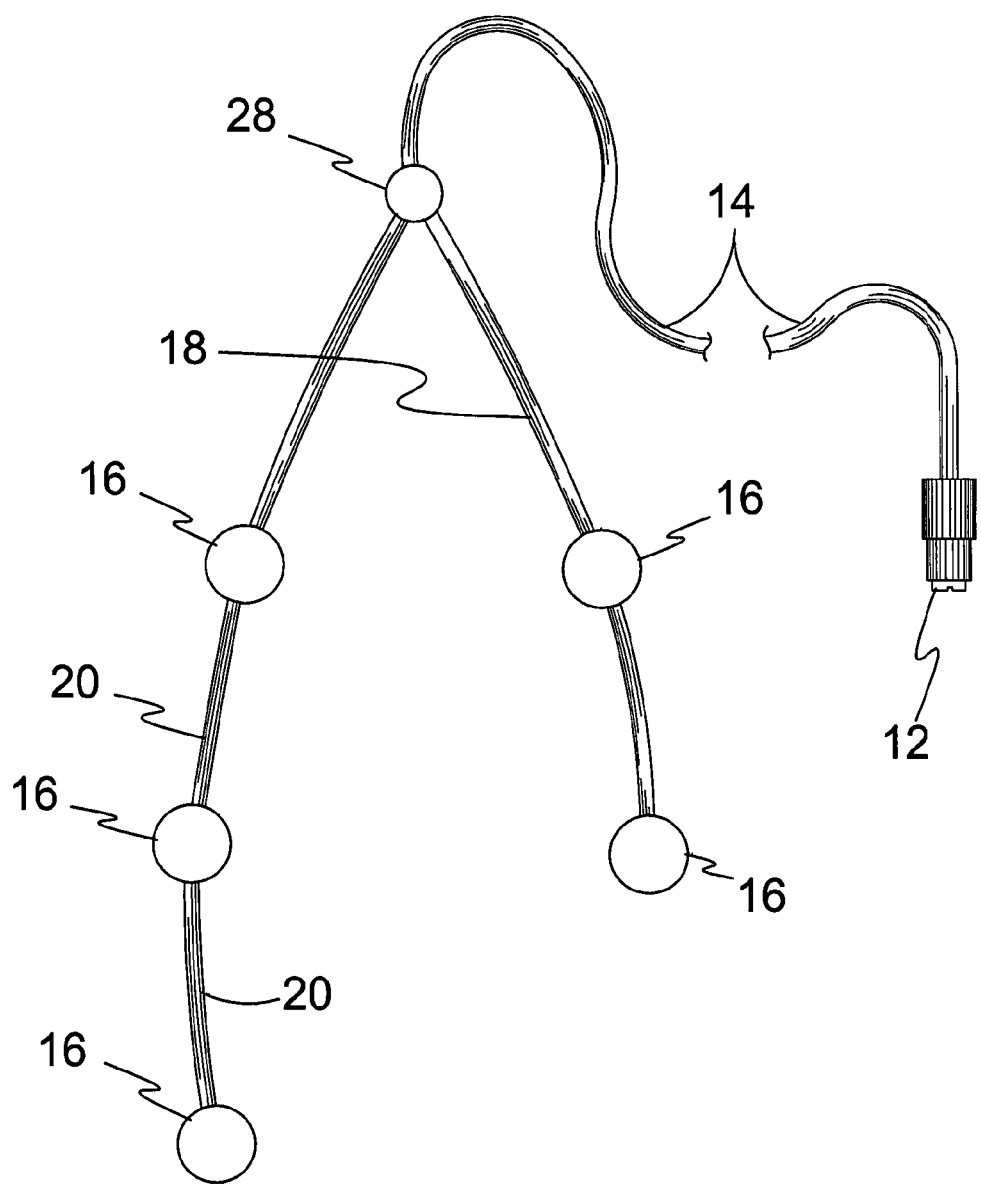
Figure 6:
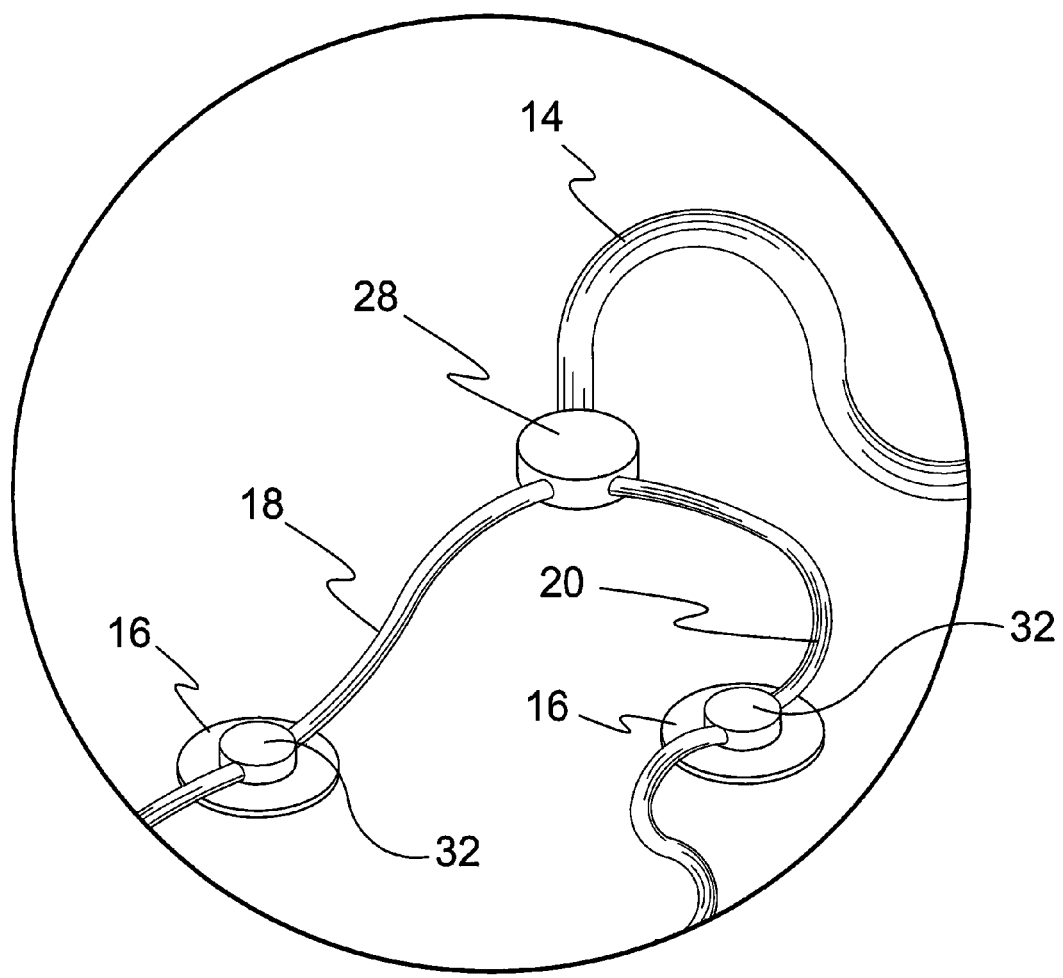
Figure 7:
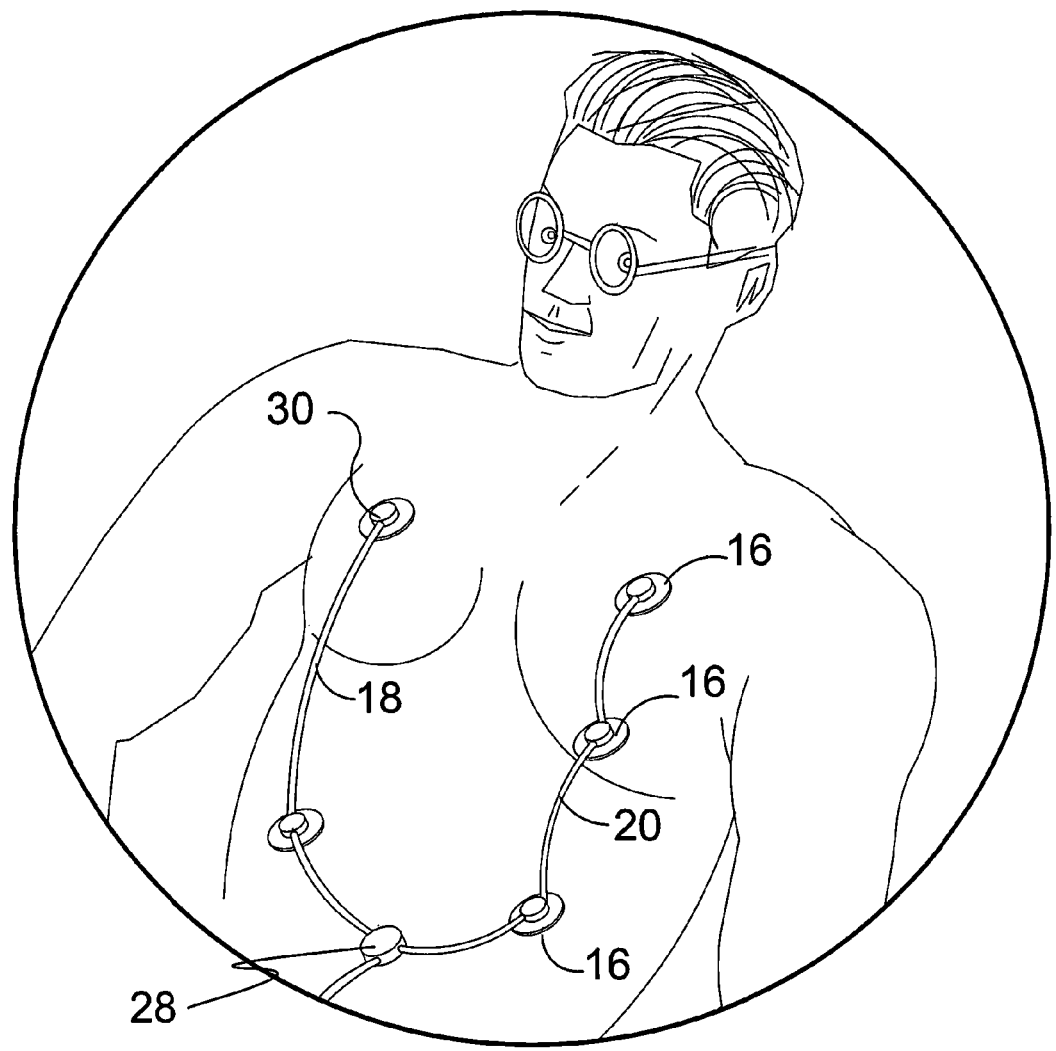
Figure 7A:
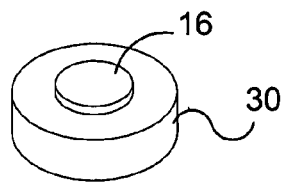
Figure 7B:
Figure 7C:
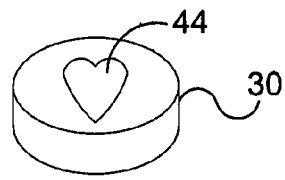
Figure 7D:
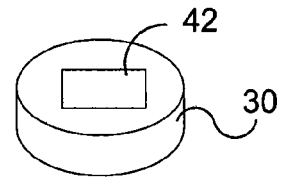
Figure 7E:
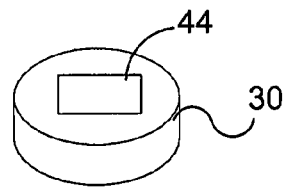

In order that the invention may be more fully understood, it will now be described, by way of example, with reference to the accompanying drawing in which:

FIG. 1 is an example of prior art.
FIG. 2 is a top view of the present invention.
FIG. 3 is a perspective view of the present invention.
FIG. 4 is an illustrative view of the present invention in use.
FIG. 5 is a rear view of the present invention.
FIG. 6 is a detailed view of the present invention.
FIG. 7 is an illustrative view of a different use of the present invention in use.
FIG. 7A is a detailed view of a node.
FIG. 7B is another detailed view of a node.
FIG. 7C is yet another detailed view of a node.
FIG. 7D is yet another detailed view of a node.
FIG. 7E is yet another detailed view of a node.

LIST OF REFERENCE NUMERALS

With regard to reference numerals used, the following numbering is used throughout the drawings.

10 Present Invention
12 Connector
14 Root Cable
16 Electrode Discs
18 First Branch Cable
20 Second Branch Cable
22 Third Branch Cable
24 Fourth Branch Cable
26 Fifth Branch Cable
28 Cable Connector
30 Node
32 Connection Socket
34 Proximal Node
36 Intermediate Node
38 Distal Node
40 Indicia
42 Color-Coding
44 Braille

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

An example of the prior art is seen in FIG. 1. Electrocardiographic cables or EKG cables are used in intensive care units and operating rooms. It has a root cable 14. The distal end of the root cable has a connector 12 thereon. The proximal end of the root cable 14 has a cable connector 28 for joining five individual branch cables 18, 19, 20, 21, 22. As a general rule each of the branch cables is joined to an individual electrode disc 16. This requires a nurse or physician to attach the cables to the body of a patient, which requires time. The present invention overcomes this problem by providing a cable system where the cables are well isolated and simplified into two cables, allowing the attachment to be easier and quicker.

The present invention 10 is represented in FIGS. 2-7. Below is a detailed discussion of the present invention with respect to FIGS. 2-7.

As seen in FIG. 3 the EKG cable has a first branch cable 18, a second branch cable 20, and a root cable 14. A cable connector 28 joins the three cables. The root cable 14 has a connector 12 so that the cable can be connected to an EKG machine. The first branch cable 18 has two electrical connection nodes. The second branch cable 20 has three electrical connection nodes. Each of the five nodes is configured to receive an electrode disc 16. It is contemplated that each of the nodes will have two opposed sides, where each of the opposed sides has a connection socket 32 for receiving an electrode disc 16. The two sides will be referred to as a first side and a second side. On a cable with five nodes, there will be a total of ten connection sockets 32, one in each of the five first sides and one in each of the five second sides. It is contemplated that when it is desired to receive more signals from the patient the cable can have more than five nodes and would therefore have more connection sockets 32. The important feature is that each of the nodes has two connection sockets 32, one in the first surface and one in the second surface. It is this feature that allows the user to deploy the EKG cable in either a downward direction as seen in FIG. 4 or an upward direction as seen in FIG. 7. The user has several ways to employ the EKG cable. The user can first lay the cable on the patient in the desired upward or downward direction. This provides the user a visual indication of where the electrodes will need to be placed on the patient so that the EKG cable can be connected to the electrodes 16 in the event that the electrodes 16 are secured to the patient before they are connected to the nodes on the EKG cable. In the alternative the electrode discs 16 will be secured prior to deployment. The user may secure all the electrode discs 16 in the connection sockets 32 on the first side of each node, one in each connection sockets 32. Then the cable will be deployed on the patient as seen in FIG. 4. To reverse the deployment direction, the user will place all the electrode discs 16 in the connection sockets 32 of the second side of each node, one in each connection socket 32. Then the cable will be deployed on the patient as seen in FIG. 7.

The nodes as seen in FIGS. 2-7 are shown with a smaller diameter than that of the electrode discs 16. It has been contemplated that the nodes may be provided with a diameter that is larger than that of the electrode disc 16 (see FIG. 7A). The larger diameter nodes will retain the EKG cable in a stable position on the user prior to securing the electrode discs 16 to the user. Larger nodal surfaces will provide a larger area for the disposition of appropriate indicia 40 thereon. The user will have an immediate visual indication showing that the EKG cable has been placed correctly or incorrectly. It is envisioned that the indicia 40 can be in the form of letters such as A or L. The A indicates an arm reading and the L indicates a leg reading. Thus the user will immediately see that the electrode discs 16 are in the proper location ensuring the receivers in the EKG machine receive the proper signal. To understand how the indicia 40 is disposed on the first and second nodal surfaces, specific attention is drawn to FIGS. 4 and 7. Looking first at FIG. 4, it will become apparent how the indicia 40 is located on the second surface of each of the nodes. As identified previously, the first sides of each of the nodes face the patient and cannot be seen in the figure. The second sides of the nodes face away from the patient. We are able to see the second sides of each of the nodes since they are facing upwards. The first branch cable 18 has two nodes, a proximal node 34, which is closer to the cable connector 28, and a distal node 38, which is disposed on or near the distal end of the first branch cable 18. The second side (upward facing) of the proximal node 34 could have the letter A indicating an arm reading. If further recognition is desired; the second surface could have the letters RA for indicating right arm since it is attached adjacent the right arm of the patient. The distal node 38 of the first branch cable 18 could have the letter L indicating a leg reading. If further recognition is desired it could have the letters RL indicating a right leg reading. The proximal node 34 on the second branch cable 20 could have the letter A or the letters LA. The distal node 38 of the second branch cable 20 could have the letter L or LL. The intermediate node 36 on the second branch cable 20 could have the letter V indicating heart reading. Now looking at FIG. 7, it will become apparent how the indicia 40 is disposed on the first side of each of the nodes. The first side of each node is facing up since the EKG cable orientation is reversed. The EKG cable is flipped over where the first sides are now upward facing and the second sides are now facing the patient. This is apparent since the root cable 14 is now positioned proximate the abdomen of the patient when previously it was proximate the head of the patient. The first side of the distal node 38 of the first branch cable 18 could have the letter A or the letters RA. The first side of the proximal node 34 of the first branch cable 18 could have the letter L or letters RL. The distal node 38 of the second branch cable 20 could have the letter A or LA. The first side of the proximal node 34 of the second branch cable 20 could have the letter L or letters LL. The first and second sides of the intermediate node 36 could have the letter V. It can now be seen that the indicia 40 on the first side of a node is different from the indicia 40 on the second side of the same node (except the intermediate node in the second branch cable). This enables the user to position the EKG cable in either an upward or downward direction. It is also envisioned that the indicia 40 may be in the form of a picture or symbols. The pictures or symbols would show a representation of an arm, a leg, or a heart (see FIG. 7C). It is also possible to employ color-coding on the nodes (see FIG. 7D). The first and second surfaces of each node could employ a distinct color to identify the correct location. It is also envisioned that the EKG cable may have tactile indicia such as Braille 44 so that a user with limited sight can employ the EKG cable and electrodes 16 properly (see FIG. 7E).

It should now be apparent that the connection sockets 30 in the first and second surfaces of a single node (with the exception of the intermediate node on the second branch cable) are wired to different terminals of the connector on the distal end of the root cable 14, which joins the cable to the EKG machine. The intermediate node 36 will always send the V or heart signal. From the following it will become apparent how the individual connection sockets 32 are connected or wired in the cable with respect to the distal 38 and proximal nodes 34. Looking first at FIG. 4, the first surface of each node is facing the patient. The second surface of each node is facing upward. The connection socket 30 in the first surface of the distal node on the first branch cable 18 is connected to an electrode 16 attached to the patient. This connection socket 30 will be connected or wired in the cable to the RL terminal in connector 12. The connection socket 30 in the first surface of the proximal node 32 on the first branch cable 18 is also connected to the electrode attached to the patient. This connection socket 30 will be connected or wired in the cable to the RA terminal in connector 12. The connection socket 30 in the first surface of the distal node 38 on second branch cable 20 is connected to an electrode 16 attached to the patient. This connection socket will be connected or wired in the cable to the LL terminal in connector 12. The connection socket 30 in the first surface of the proximal node 34 on the second branch cable 20 is also connected to an electrode 16 attached to the patient. This connection socket 30 will be connected or wired in the cable to the LA terminal in connector 12.

Looking now at FIG. 7, the second surface of each node is now facing the patient since the EKG cable has been flipped over. The first surface of each node is now facing upward. The connection socket 30 in the second surface of the distal node 38 on first branch cable 18 is connected to an electrode 16 attached to the patient. This connection socket will be connected or wired in the cable to the RA terminal of connector 12. The connection socket 30 in the second surface of the proximal node 34 on the first branch cable 18 is also connected to an electrode 16 attached to the patient. This connection socket 30 will be connected or wired in the cable to the RL terminal of connector 12. The connection socket 30 in the second surface of the distal node 38 on second branch cable 20 is connected to an electrode 16 attached to the patient. This connection socket 30 will be connected or wired in the cable to the LA terminal of connector 12. The connection socket 30 in the second surface of the proximal node 34 on the second branch cable 20 is also connected to an electrode 16 attached to the patient. This connection socket 30 will be connected or wired in the cable to the LL terminal in connector 12. The connector 12 will have at lease five terminals one for each of the five nodes. It is envisioned that the connector can have a greater number of terminals than the number of nodes on the EKG cable.

I claim:

1. An EKG cable for connection to an EKG machine so that the machine can take the EKG of a patient, the EKG cable comprising: a root cable with distal and proximal ends, the proximal end of the root cable being joined to a cable connector, the distal end of the root cable being joined to a connector for connection to an EKG machine, two branch cables being connected to said cable connector, wherein a first of said branch cables has two nodes disposed thereon, a proximal node which is disposed on said first cable proximal the cable connector and a distal node which is disposed on said first cable on or adjacent a distal end, wherein a second of said branch cables has three nodes disposed thereon, wherein each of said nodes has an upper surface and a lower surface disposed opposite the upper surface, wherein each of the surfaces of all of the nodes has a connection for receiving an electrode disc, wherein the upper surface of a first of one of said nodes has indicia for indicating connection to an electrode disc selected from the group consisting of RA, RL, LA, and LL; and said lower surface of the first one of said nodes has indicia which indicates connection to an electrode disc which is different from the indicia on the upper surface of the first one of said nodes.

2. The EKG cable of claim 1, wherein a second one of said nodes has indicia for indicating connection to an electrode disc selected from the group V, a heart symbol, and a picture of a heart.

3. The EKG cable of claim 1, wherein the upper surface of a second one of said nodes has indicia for indicating connection to an electrode disc selected from the group consisting of RA, RL LA, and LL; and the indicia on the upper surface of the first node is different from the indicia on the upper surface of the second node.

4. The EKG cable of claim 3, wherein the upper surface of a third of one of said nodes has indicia for indicating connection to an electrode disc selected from the group consisting of RA, RL LA, and LL; and the indicia on the upper surface of the three nodes are different from each other.

5. The EKG cable of claim 4, wherein the upper surface of a fourth one of said nodes has indicia for indicating connection to an electrode disc selected from the group consisting of RA, RL LA, and LL; and the indicia on the upper surface of the four nodes are different from each other.

6. The EKG cable of claim 5, wherein the lower surface of said fourth node has indicia which is different from the indicia on said upper surface of said fourth node.

7. The EKG cable of claim 4, wherein the lower surface of said third node has indicia which is different from the indicia on said upper surface of said third node.

8. The EKG cable of claim 3, wherein the lower surface of said second node has indicia which is different from the indicia on said upper surface of said second node.

9. An EKG cable which can be deployed on a patient in both and upward and a downward direction, the cable comprising: a root and two branches, said root and said two branches being joined by a cable connector, wherein a first of said branches has two nodes disposed thereon, wherein each node of said first branch has two connections each capable of being connected to an electrode disc, and wherein the second of said branches has three nodes disposed thereon, wherein each node of said second branch has two connections each capable of being connected to an electrode disc, wherein each of the nodes on said first and said second branches has an upper surface and a lower surface disposed opposite the upper surface, wherein a first node on the first branch has indicia disposed on its upper surface selected from the group consisting of RA, RL, LA, and LL; and wherein the lower surface of said first node has indicia which is different from the indicia on said upper surface of said first node.

10. The EKG cable of claim 9, wherein the upper surface of a second one of said nodes has indicia for indicating connection to an electrode disc selected from the group consisting of RA, RL LA, and LL; and the indicia on the upper surface of the first node is different from the indicia on the upper surface of the second node.

11. The EKG cable of claim 10, wherein the indicia on the upper surface of a third of said nodes has indicia for indicating connection to an electrode disc selected from the group consisting of RA, RL, LA, and LL; and the indicia on the upper surface of the three nodes are different from each other.

12. The EKG cable of claim 11, wherein the upper surface of a fourth one of said nodes has indicia for indicating connection to an electrode disc selected from the group consisting of RA, RL LA, and LL; and the indicia on the upper surface of the four nodes are different from each other.

13. An EKG cable comprising a root cable, at least two branch cables connected to said root cable, wherein each of the branch cables has a plurality of nodes disposed thereon, wherein each of said nodes is configured with two connections, each connection capable of being connected to an electrode disc, wherein each of the nodes has an upper surface and a lower surface opposite said upper surface, where each of said upper and lower surfaces has indicia disposed thereon for indicating connection to an electrode disc, and the indicia on the upper surface of a respective node is different from the indicia on the lower surface of the same node.

14. The EKG cable of claim 13, where the indicia on the upper and lower surfaces of each of the nodes is Braille.

15. The EKG cable of claim 14, wherein each of the upper and lower surfaces of each of the nodes is color coded.

16. The EKG cable of claim 13, wherein indicia on the upper and lower surfaces of each of the nodes is a picture or a symbol.

17. The EKG cable of claim 13, wherein the plurality of nodes on a first branch cable comprise a proximal node and a distal node, the distal node being disposed at or near a distal end of the first branch cable and the proximal node being closer to the root cable than the distal node, wherein the indicia on the upper surface of said distal node is the same as the indicia on the lower surface of said proximal node.

18. The EKG cable of claim 13, wherein the plurality of nodes on a second branch cable comprise a proximal node, an intermediate node, and a distal node, the distal node being disposed at or near a distal end of the second branch cable, the proximal node being closer to the root cable than the distal node and the intermediate node being disposed intermediate the proximal and the distal nodes, wherein the indicia on the upper surface of said distal node is the same as the indicia on the lower surface of said proximal node.

19. The EKG cable of claim 18, wherein the indicia on the upper surface of the intermediate node is the same as the indicia on the lower surface of the intermediate node, and the indicia on the intermediate node is different from the indicia on any of the other nodes.

* * * * *